(12) United States Patent
Sjöstedt

(10) Patent No.: US 9,192,771 B2
(45) Date of Patent: Nov. 24, 2015

(54) IMPLANTABLE MEDICAL DEVICE

(75) Inventor: Johan Sjöstedt, Hässelby (SE)

(73) Assignee: ST JUDE MEDICAL AB, Jarfalla (SE)

( * ) Notice: Subject to any disclaimer, the term of this patent is extended or adjusted under 35 U.S.C. 154(b) by 1954 days.

(21) Appl. No.: 12/066,954

(22) PCT Filed: Sep. 29, 2005

(86) PCT No.: PCT/SE2005/001445
§ 371 (c)(1),
(2), (4) Date: Mar. 14, 2008

(87) PCT Pub. No.: WO2007/037728
PCT Pub. Date: Apr. 5, 2007

(65) Prior Publication Data
US 2008/0262563 A1    Oct. 23, 2008

(51) Int. Cl.
*A61N 1/375*    (2006.01)
(52) U.S. Cl.
CPC ............................. *A61N 1/3752* (2013.01)

(58) Field of Classification Search
USPC ............... 607/1–2, 36, 115; 174/50.5, 50.52; 439/566, 736
See application file for complete search history.

(56) References Cited

U.S. PATENT DOCUMENTS

| | | |
|---|---|---|
| 4,182,345 A | 1/1980 | Grose |
| 5,076,270 A | 12/1991 | Stutz, Jr. |
| 5,336,246 A | 8/1994 | Dantanarayana |
| 5,851,221 A | 12/1998 | Rieder et al. |
| 5,871,514 A | 2/1999 | Wiklund et al. |
| 2002/0107555 A1 | 8/2002 | Rusin et al. |
| 2004/0093038 A1 | 5/2004 | Biggs et al. |
| 2006/0041282 A1 | 2/2006 | Hornsfeldt et al. |

*Primary Examiner* — Deborah Malamud

(57) ABSTRACT

In an implantable medical device and a method for assembly thereof, a hermetically sealed housing encloses electronic circuitry and has a housing fastener part that is formed of metal and that protrudes from the housing. A per-fabricated header, for receiving conducting leads and for connecting the conducting leads to the electronic circuitry, has a header fastener part also formed of metal. The header is fastened to the housing by metal-to-metal welding of the housing fastener part and the header fastener part at a distance from the housing.

15 Claims, 3 Drawing Sheets

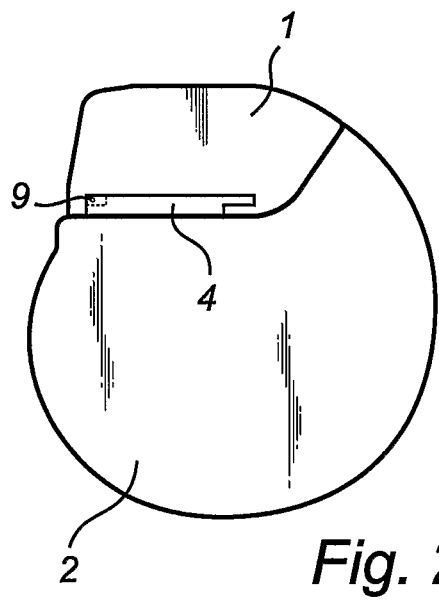 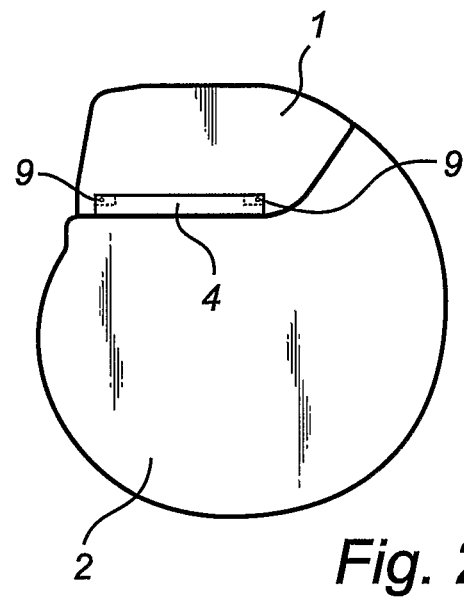
Fig. 2a    Fig. 2b
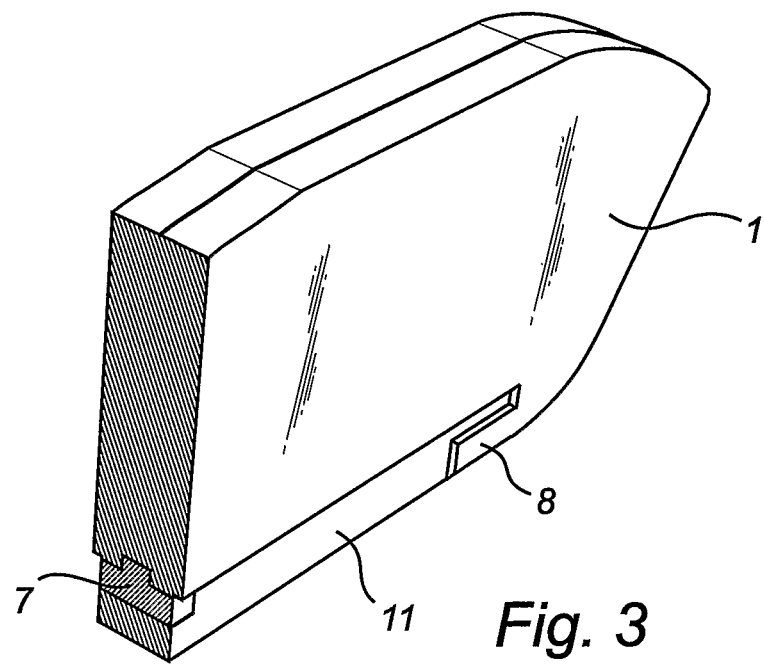
Fig. 3

IMPLANTABLE MEDICAL DEVICE

BACKGROUND OF THE INVENTION

1. Field of the Invention

The present invention relates to an implantable medical device and to a method for assembling an implantable medical device. It further relates to a pre-fabricated header and to a hermetically sealed housing for use in an implantable medical device.

The present invention is applicable to a variety of implantable medical devices of the type having a pre-fabricated part to be coupled to a housing part. Examples of such devices are heart stimulators such as cardiac pacemakers and implantable cardioverter-defibrillators (ICD's). However, the invention and its background will be described herein in terms of a specific example of such implantable devices, namely cardiac pacemakers.

2. Description of the Prior Art

Present day cardiac pacemakers are typically designed to be implanted in a "pocket" of fatty tissue near the patient's upper chest or lower abdomen. Accordingly, electronic circuits within the pacemaker are hermetically sealed within a housing made of a material that is compatible with body tissue. Electrical connection from the outside with the electronic circuits within the hermetically sealed housing is accomplished via a connector assembly, often referred to as a header or header assembly, that is arranged on the pacemaker housing. Feedthrough terminals that pass through the hermetically sealed housing are connected with the pacemaker electronic circuits in the housing and with a lead pin receptacle in the connector assembly. At a proximal end, a lead conductor is provided with a lead pin for being received in the connector receptacle and at a distal end, the lead conductor is provided with electrodes for electrical tissue stimulation at the desired tissue location.

In order to ensure good electrical contact between the circuits within the housing and the outside, it is desirable to achieve a strong and reliable joint between the header and the housing.

Traditionally, a pacemaker is assembled by positioning the components of the header in connection with the hermetically sealed housing in a mold, adding a molding compound and molding the header on top of the hermetically sealed housing. A disadvantage with this known method is that it is complex and time consuming.

According to another known pacemaker design, as for instance disclosed in U.S. Pat. No. 4,182,345, the header is pre-molded. On the housing, there are projecting posts provided with through holes. In the header, complementary holes for receiving the posts and through going holes are provided. The through going holes of the header are arranged such that they aligned with the through going holes of the posts when the header is mounted on the housing. The header is locked to the housing by cross pins passing through the aligned through going holes of the post and the header. A disadvantage with this known device is that only very small tolerances are acceptable and that, in view of the size of the components, the mounting operation will be complicated and difficult.

In United States Patent Application Publication No. 2004/0093038 a pre-molded header assembly for an implantable medical device is disclosed. The bottom wall of the header is supported by a support plate of metal and retained in place in the header by a peripheral undercut. The housing of the implantable medical device has a planar upper surface. The pre-molded header can be mounted to the medical device by welding the support plate to the upper surface of the housing.

A problem with this known device is that, the welding operation may cause a severe heat development unless it is very carefully performed. As a consequence, the polymeric material of the header may melt and the conductor arrangements of the header may be damaged. Furthermore, the heat may cause a leakage in the hermetically sealed housing. If the welding operation fails, both the header and the housing must be discarded.

SUMMARY OF THE INVENTION

An object of the present invention is to provide an implantable medical device and a method for assembling an implantable medical device, the improved medical device having an improved structure for fastening a pre-fabricated header to a hermetically sealed housing compared to the prior art devices. It is also an object of the present invention to provide a pre-fabricated header and a hermetically sealed housing for use in such a medical device.

The implantable medical device according to invention has a hermetically sealed housing enclosing electronic circuitry and pre-fabricated header for receiving conducting leads and for connecting the conducting leads to the electronic circuitry. The header includes a header fastener part formed of metal and the housing includes a housing fastener part formed of metal. Furthermore, the housing fastener part protrudes from the housing. The housing fastener part and the header fastener part are connected such that the header is fastened to the housing, wherein the housing fastener part and the header fastener part are connected by a connecting weld at a distance from the housing.

Due to the header fastener part and the housing fastener part being of metal, a metal-to-metal welded joint can be used, thus fastening the header to the housing in a strong and reliable manner. Furthermore, since the housing fastener part protrudes form the housing, the welding can be performed at a distance from the housing, such that the heat experienced by the housing is reduced compared with welding directly to the housing. In addition, due to the extension of the housing fastener part and the connecting weld, tolerance problems regarding the positioning of the header fastener part are reduced. Furthermore, the welded joint according to the invention is easy to inspect and, in several directions, relative large tolerances are acceptable regarding the dimension and position of the fastening parts.

The method according to the invention for assembling an implantable medical device, includes the steps of providing a hermetically sealed housing enclosing electronic circuitry and having a housing fastener part, which is formed of metal and which protrudes from the housing, providing a pre-fabricated header for receiving conducting leads and for connecting the conducting leads to the electronic circuitry and having a header fastener part which is formed of metal, and the step of fastening the header to the housing by welding the header fastener part to the housing fastener part by metallic welding at a distance from the housing.

As used herein, the term "welding" encompasses all metallic welding including brazing and soldering.

The metallic housing fastener part and the metal member of the header fastener part can be of any metal suitable for metallic welding and compatible with body tissue, for example titanium.

According to the invention, both the housing fastener part and the header fastener part are made of metal. When the header and the housing are positioned for being attached together, the respective fastener parts are in a position relative each other that is suitable for metallic welding thereof. Furthermore, the fastener parts are located such that they are accessible for the welding operation.

According to one embodiment of the invention, the header fastener part has an exposed portion at least one side of the header. The welding operation is thereby facilitated.

According to the invention, the housing fastener part protrudes from the housing such that the header fastener part is not directly welded to the housing. However, this does not exclude the housing fastener part is integral with the housing, such as for example an reinforced, thicker portion of the housing. A suitably reinforced portion can be sufficiently to guarantee that the housing will not be damaged due to the heat development during the welding operation. The housing fastener part can also include a metal member that is integral with the housing but still extends away from the housing to allow welding at a distance from the housing.

According to the invention, the header fastener part can be mounted in the header in any suitable manner depending on how the header is fabricated. The header fastener part need not be mounted fixedly in the header, it is sufficient if the header and the housing are fixedly locked when the header fastener part has been welded to the housing fastener part. If, as according to one embodiment of the invention, the header fastener part is fixedly mounted in the header, the pre-fabricated header including the header fastener part can be easily handed and transported prior to and during assembly without risking loss of the header fastener.

According to one embodiment of the invention the housing fastener part includes a metal member attached to the housing. In this embodiment, the housing fastener part constitutes a separate detail attached to the housing by welding. Of course, any other suitable attachment is also possible, for example screws, nails or glue. One advantage with this embodiment is that the hermetically sealed compartment of the housing is not affected when the header is welded to the metal element of the housing fastener part. Consequently, it is possible to leak test the hermetically sealed housing after the attachment of the metal member to the housing before the fastening of the header. If the housing should prove to be defect, it is only necessary to discard the housing.

According to one embodiment of the housing, the housing fastener part protrudes from a header facing side of the housing towards the header.

According to one embodiment of the invention, the surface of the header fastener part and the surface of the housing fastener part that are connected by the connecting weld are arranged in a plan perpendicular to a connecting plane of the housing and the header. This orientation of the fastening part is advantageous regarding tolerances.

According to one embodiment of the invention, the housing fastener part extends along a substantial part of the surface of the housing that faces the header when the header is connected with housing. Thereby tolerance problems regarding the positioning of the header fastener part in the direction of the extension of the housing fastener part are avoided.

According to one embodiment of the invention, the housing fastener part has an extension both along the housing, more precisely along the long side of the surface facing the header when the housing is fastened to the header, and in the direction of the connecting movement of the header. Thereby, tolerance is an issue in one dimension only, i.e. in the sideway direction. The surfaces of the housing fastener part and the header fastener part must be sufficiently close to allow welding together thereof.

According to one embodiment of the invention, the housing fastener part includes several metal members cooperating with a single metal element of the header fastener part. According to another embodiment of the invention, the header fastener part includes several metal elements cooperating with a single member of the housing fastener part. According to another embodiment of the invention, the housing fastener part includes several metal members cooperating with several metal elements of the header fastener part.

Regardless of the number of cooperating metal elements and metal members, the header can be welded to housing in a single or in several locations. An advantage of using several welding locations is that a strong joint is achieved, since forces exerting a torque on the joint are better distributed. Furthermore, the header will be subjected to less heat.

According to one embodiment of the invention, the header is pre-molded. In this embodiment, the header fastener part can be insert-molded in the header together with the other components of the header. It is also possible to press the header fastener part into the header after molding. An advantage with this embodiment is that the invention is easily incorporated in a manufacturing process of the prior art.

According to one embodiment of the invention, the prefabricated header is formed, for example molded, of an electric insulating material compatible with body tissue, such as polyurethane or epoxy resins.

BRIEF DESCRIPTION OF THE DRAWINGS

FIG. 1b is a perspective view of the implantable medical device according to FIG. 1a.

FIG. 2a is a side view of the implantable medical device according to FIG. 1a.

FIG. 2b is a side view of an implantable medical device according to a second embodiment of the invention.

FIG. 3 is a perspective view of a header according to a third embodiment of the implantable medical having a transversal cut at a header fastener part

DESCRIPTION OF THE PREFERRED EMBODIMENTS

Figure 1A:
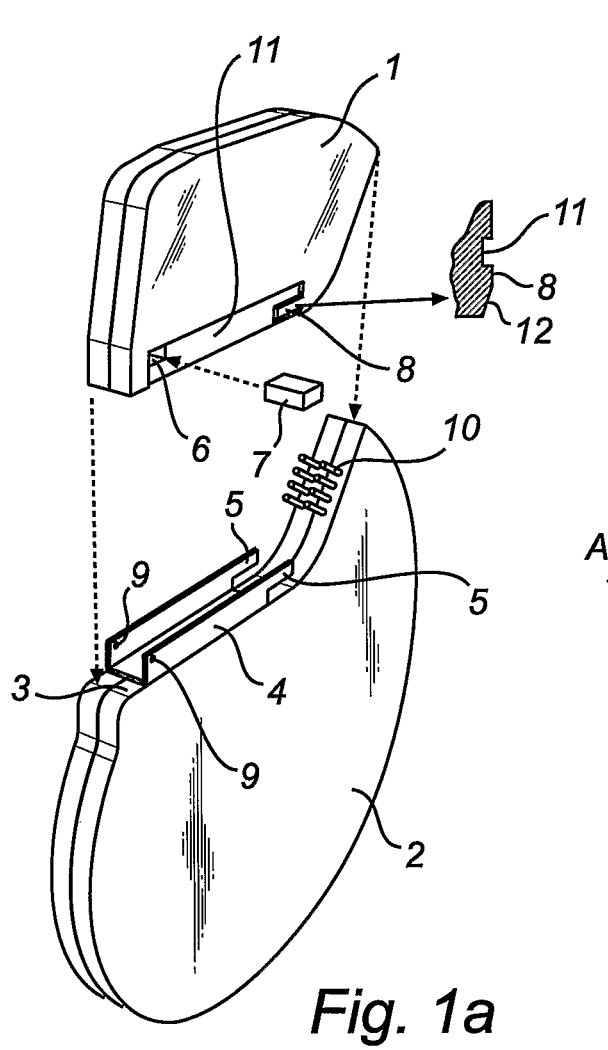
FIG. 1a is an exploded view of an implantable medical device according to a first embodiment of the invention.
Figure 1B:
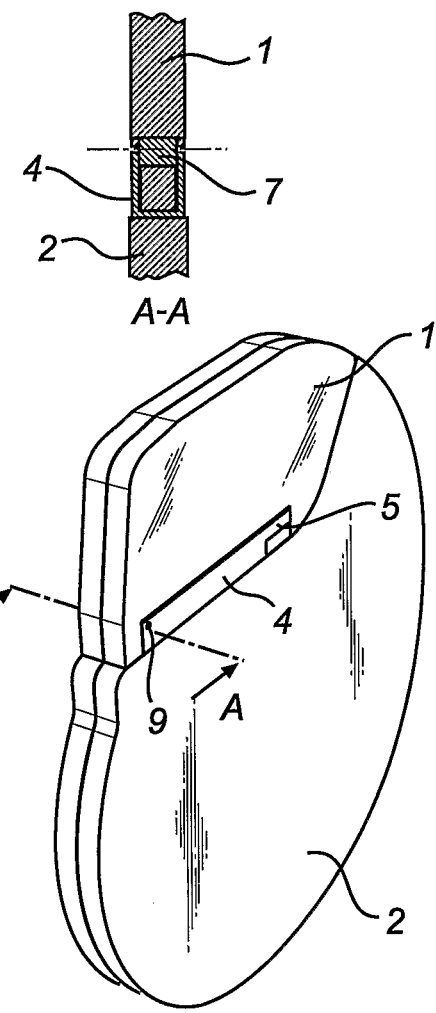

With reference to FIGS. 1a, 1b and 2a, an implantable medical device according to a first embodiment of the invention is shown. The implantable medical device according to the example is a pacemaker. The pacemaker includes a prefabricated header in the form of a pre-molded header 1 made of polyurethane. The pacemaker further includes a hermetically sealed housing 2 formed of titanium. The housing 2 is provided with feedthrough terminals 10 that are electrically connected to the electronic circuits inside the hermetically sealed housing 2. The header 1 is provided with a connector receptacle for receiving a connector pin at the proximal end of a pacing lead (not shown).

A housing fastener part formed of metal and in the form of a U-shaped bracket 4 is attached to the housing 2 by welding. The bracket 4 is attached to a surface 3 of the housing 2 which faces the header 1 when the header 1 and the housing 2 are fastened together. The bracket 4, extends along a mayor portion of the surface 3. The two sides of the U-shaped bracket 4 protrude from the housing 2 and extends towards the header 1 in a direction that is perpendicular to the surface 3.

At one end of the U-shaped bracket 4, each side of the U-shaped bracket 4 is provided with an undercut leaving a finger portion 5. At the other end of the U-shaped bracket 4, each side of the U-shaped bracket is provided with a through hole 9.

The header 1 is provided with a through going hole 6. A header fastener part in form of a metal element 7 is inserted in the through going hole 6. The metal element 7 is exposed at each side of the header 1 at each end of the through going hole 6.

The thickness of the header 1 at the end facing the housing 2 when the header 1 is mounted to the housing 2, is slightly less than the distance between the two sides of the U-shaped bracket 4, so that the header 1 will fit between the two sides of the U-shaped bracket 4. This reduced thickness portion 11 of the header 1 is made slightly larger than the size of the U-shaped bracket 4 to avoid tolerance problems. At one end of the reduced thickness portion 11, a hook portion 8 with full thickness extends into the reduced thickness portion 11. Between the hook portion 8 and the reduced thickness portion 11, the header 1 is provided with a bevelled portion 12.

The medical device according to the invention can be assembled in the following way.

The rod 7 is inserted in the through going hole 6 of the header 1 and the header 1 is lowered towards the housing 2. Carefully, the feedthrough terminals 10 of the housing 1 are electrically connected to the connector receptacle (not shown) in the header 1.

Thereafter the header 1 is lowered further and placed in position between the two sides of the U-shaped bracket 4 on the housing 2. Due to the bevelled portion 8, the hook portion 11 will slide in between the finger portions 5 and the hook portion 8 will snap into the reduced thickness portion 11.

The exposed ends of the metal element 7 will slide in between the two sides of the U-shaped bracket 4. Each end surface of the metal element 7 will face one side respectively. Due to the extension of the two sides along and perpendicular to the surface 3, the requirements for an exact relative position between the header and the housing 2 are not severe and quite large tolerances can be allowed. A remaining limiting feature is that the ends of the rod 7 must fit between the two sides of the bracket 4 and not end up too far from the sides.

Finally, the ends of the metal element 7 are welded to one side of the U-shaped bracket respectively by laser welding. The weld can be executed through the holes 9 in the bracket 4.

Due to the finger portion 5 of the U-shaped bracket 4 in cooperation with the hook portion 8 of the header 1, the header 1 is fastened to the housing by welding in only two discrete locations which are located at a distance from the housing. Consequently, risk that the header 1 or the housing 1 are damaged by the heat produced by the welding operation is very small. At same time, a tolerance allowing joint is achieved. Due to the welding and the mechanical locking being provided at each end of the U-shaped bracket, the joint will also be resistant to torque forces.

With reference to FIGS. 2b-5 in the following alternative embodiments of the invention will be described. In the figures, those parts that correspond to parts shown in FIGS. 1a, 1b and 2a are provided with the same reference numerals.

A second embodiment of the invention is shown in FIG. 2b. The second embodiment differs from the first described embodiment in that the U-shaped bracket 4 of the housing fastener has a constant cross section and consequently lacks the finger portions 5 of the first embodiment. Furthermore, the header 1 is provided with two through going holes 6 in which a metal element 7 is inserted respectively. The metal elements 7 are exposed at the sides of the header 1 at each end of the respective through going hole 6.

When the medical device according to the invention is assembled, the ends of each metal element 7 are welded to one side of the U-shaped bracket respectively by laser welding. The weld can be effected through the holes 9 in the bracket 4.

Consequently, the header is welded to the housing at four spaced locations. In this embodiment, the housing is fastened to header by welding only. A tolerance allowing joint is achieved with a low amount of heat transferred to the housing 2. Due to the connecting weld being provided at each end of the U-shaped bracket 4, also this the joint will be resistant to torque forces.

In FIG. 3, a third embodiment of the invention is shown, where a metal element 7 of the header fastener is shaped and fitted in the header 1 such that the metal element 7 and the header 1 are interlocked in all directions. The metal element 7 has a T-shaped cross section and is insert-moulded in a corresponding recess in the header 1. Thereby the metal element 7 of the third embodiment is prevented from falling out of the header 1 before the header has been welded to the housing 2.

Figure 4:
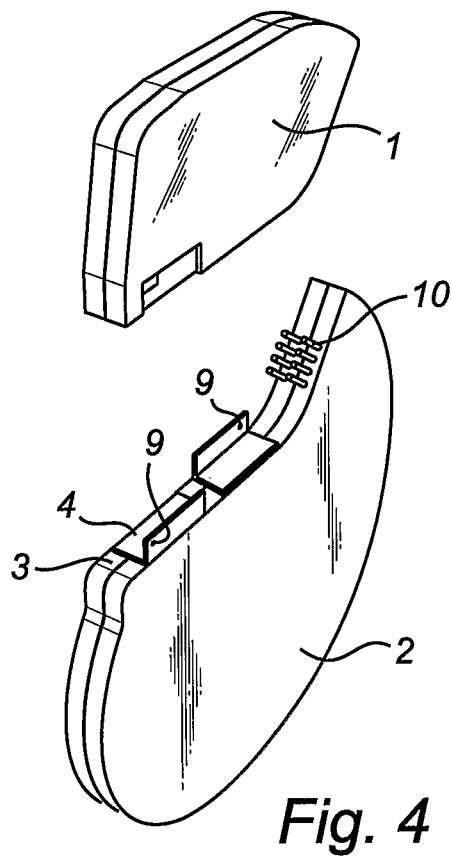
FIG. 4 is an exploded view of an implantable medical device according to a fourth embodiment of the invention.

In FIG. 4, an alternative embodiment of the housing fastener part is shown. Instead of the U-shaped bracket 4 in the previous embodiments, a housing fastener part formed of metal and in the form of two L-shaped brackets 4 is attached to the housing 2 by welding. In this embodiment, the header 1 is provided with two metal elements 7 that are arranged in corresponding recesses 6 in the header 1. The metal elements 7 do not extend through the thickness of the header 1, but protrude at one side thereof, respectively. In the mounted implantable medical device, the exposed end of each metal member 7 is welded to a corresponding L-shaped bracket 4. This will provide a joint essentially equivalent to the joint of the second embodiment.

Figure 5:
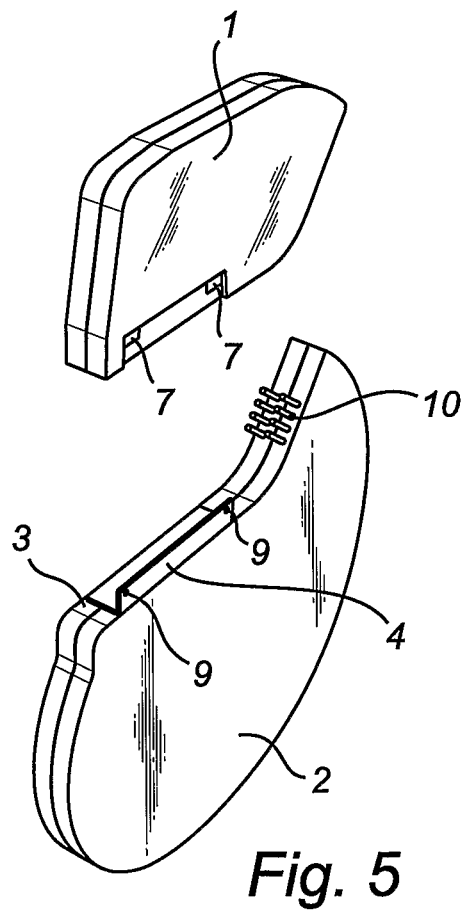
FIG. 5 is a exploded view of an implantable medical device according to a fifth embodiment of the invention.

In FIG. 5, another alternative embodiment of the housing fastener part is shown. The housing fastener part is formed of metal in the form of one L-shaped bracket 4 which is attached to the housing 2 by welding. In this embodiment, the header 1 is provided with two metal elements 7 that are arranged in corresponding recesses 6 in the header 1. The metal elements 7 do not necessarily extend through the thickness of the header 1, but are exposed at one and the same side thereof. In the mounted implantable medical device, the exposed end of each metal member 7 is welded to the L-shaped bracket 4. Although this joint may be less resistant to torque forces, this embodiment is especially easy to assemble, since the welding only has to be performed at one side.

Although modifications and changes may be suggested by those skilled in the art, it is the intention of the inventor to embody within the patent warranted heron all changes and modifications as reasonably and properly come within the scope of his contribution to the art.

I claim as my invention:
1. An implantable medical device comprising:
   a hermetically sealed housing enclosing electronic circuitry and a pre-fabricated header configured for receiving conducting leads and comprising electrically conductive elements that electrically connect the conducting leads to the electronic circuitry;
   said housing comprising a housing fastener part formed of metal and protruding from the housing;
   said header comprising a header fastener part formed of metal and being separate from and independent of said electrically conductive elements;

said housing fastener part and the header fastener part being connected to mechanically fasten and fixedly secure the header to the housing; and said housing fastener part and the header fastener part being connected by a metal-to-metal connecting weld located at a distance from the housing.

2. The implantable medical device according to claim 1, wherein the housing fastener part protrudes from a header facing side of the housing towards the header.

3. The implantable medical device according to claim 2, wherein the housing fastener part is welded to the header fastener part in a direction essentially parallel with the header facing side of the housing.

4. The implantable medical device according to claim 1, wherein the housing fastener part extends along the header facing side of the housing to allow for tolerances between the housing fastener part and the header fastener part.

5. The implantable medical device according to claim 1, wherein the housing fastener part includes a separate metal element attached to the housing.

6. The implantable medical device according to claim 5, wherein the housing fastener part comprises a U-shaped bracket having the interconnecting part attached to the housing and having the sides extending towards the header.

7. The implantable medical device according to claim 6, wherein the metal element is shaped and fitted in the header such that the metal element and the header are interlocked in all directions.

8. The implantable medical device according to claim 7, wherein the metal element has a T-shaped longitudinal cross section.

9. The implantable medical device according to claim 1, wherein the header fastener part and the housing fastener part are connected by a connecting weld at discrete points.

10. The implantable medical device according to claim 9, wherein the header fastener part includes at least one metal element extending transversally through the header for being welded to the housing fastener part on both sides of the header.

11. The implantable medical device according to claim 1, wherein the lateral sides of the header are displaced inwardly in relation to the lateral sides of the housing for giving an even surface after application of a silicon cover.

12. The implantable medical device according to claim 1, wherein the header is pre-molded.

13. A pre-fabricated header, for use in an implantable medical device comprising a hermetically sealed housing enclosing electronic circuitry, for receiving conducting leads, and said housing comprising electrically conductive elements that electrically connect the conducting leads with the electronic circuitry, the housing including a housing fastener part formed of metal and protruding from the housing, said header comprising:

a header fastener part, formed of metal and being separate from and independent of said electrically conductive elements and connectable to the housing fastener part to mechanically fasten and fixedly secure the header with the housing; and the header fastener part is connected to the housing fastener part by a metal-to-metal connecting weld at a distance from the housing.

14. A hermetically sealed housing enclosing electronic circuitry, for use in an implantable medical device comprising a pre-fabricated header for receiving conducting leads and comprising electrically conductive elements that electrically connect the conducting leads to the electronic circuitry, the header including a header fastener part formed of metal and being separate from and independent of said electrically conductive elements, said housing comprising:

a housing fastener part formed of metal that protrudes from the housing and which is connectable to the header fastener part to mechanically fasten and fixedly secure the housing with the header; and the housing fastener part is connected to the housing fastener part by a metal-to-metal connecting weld at a distance from the housing.

15. A method for assembling an implantable medical device, comprising the steps of:

providing a hermetically sealed housing enclosing electronic circuitry and having a housing fastener part, which is formed of metal and which protrudes from the housing;

providing a pre-fabricated header for receiving conducting leads and comprising electrically conductive elements that electrically connect the conducting leads to the electronic circuitry and having a header fastener part which is formed of metal and being separate from and independent of said electrically conductive elements; and fastening and fixedly securing the header to the housing by welding the header fastener part to the housing fastener part by metallic welding at a distance from the housing.

* * * * *